(12) United States Patent
Tan

(10) Patent No.: US 10,508,177 B2
(45) Date of Patent: Dec. 17, 2019

(54) METHOD AND DEVICE FOR PURIFYING POLYBUTYLENE TEREPHTHALATE

(71) Applicants: NATIONAL TSING HUA UNIVERSITY, Hsinchu (TW); Chang Chun Plastics Co., Ltd., Taipei (TW); Chang Chun Petrochemical Co., LTD., Taipei (TW)

(72) Inventor: Chung-Sung Tan, Hsinchu (TW)

(73) Assignees: NATIONAL TSING HUA UNIVERSITY, Hsinchu (TW); Chang Chun Plastics Co., Ltd., Taipei (TW); Chang Chun Petrochemical Co., LTD., Taipei (TW)

(*) Notice: Subject to any disclaimer, the term of this patent is extended or adjusted under 35 U.S.C. 154(b) by 85 days.

(21) Appl. No.: 15/802,445

(22) Filed: Nov. 2, 2017

(65) Prior Publication Data
US 2018/0371180 A1 Dec. 27, 2018

(30) Foreign Application Priority Data
Jun. 26, 2017 (TW) .............................. 106121301 A

(51) Int. Cl.
*C08J 3/14* (2006.01)
*C08G 63/127* (2006.01)
(Continued)

(52) U.S. Cl.
CPC ............. *C08J 3/14* (2013.01); *B01D 11/0203* (2013.01); *C07C 31/38* (2013.01); *C08G 63/127* (2013.01);
(Continued)

(58) Field of Classification Search
CPC ............ B01D 11/0203; B01D 11/0411; B01D 11/0484; C07C 31/38; C08G 63/127;
(Continued)

(56) References Cited

U.S. PATENT DOCUMENTS

| | | | | |
|---|---|---|---|---|
| 5,229,486 A | * | 7/1993 | Paul ...................... | C08G 63/89 528/480 |
| 5,554,657 A | * | 9/1996 | Brownscombe ......... | C08J 11/08 521/48 |

(Continued)

FOREIGN PATENT DOCUMENTS

| CN | 1196995 A | 10/1998 | |
|---|---|---|---|
| WO | WO-2016120429 A1 * | 8/2016 | ........... C08G 63/183 |

OTHER PUBLICATIONS

Wen Yu et al., "Purification of polybutylene terephthalate using supercritical/subcritical CO2 anti-solvent method", The Eleventh National Symposium on Supercritical Fluids, dated on Nov. 4-6, 2016, paper published by the supercritical fluids professional group from The Chemical Industry and Engineering Society of China, Xiamen, China.

*Primary Examiner* — Frances Tischler
(74) *Attorney, Agent, or Firm* — CKC & Partners Co., LLC

(57) ABSTRACT

A method for purifying polybutylene terephthalate (PBT) includes: providing or receiving initial PBT, in which oligomers and tetrahydrofuran are present; dissolving the initial PBT in hexafluoroisopropanol (HFIP) to form a solution, in which the oligomers are also dissolved in the HFIP; and contacting the solution with compressed $CO_2$ at a temperature and a pressure, thereby precipitating the purified PBT, resulting from a large portion of the oligomers are still dissolved in the HFIP, in the operation the temperature is in a range of 20° C. to 35° C., and the pressure is in a range of 900 psi to 1400 psi. A device for purifying PBT is also provided.

8 Claims, 4 Drawing Sheets

(51) Int. Cl.
*C08G 85/00* (2006.01)
*C08L 67/02* (2006.01)
*C08K 5/05* (2006.01)
*C07C 31/38* (2006.01)
*B01D 11/02* (2006.01)

(52) U.S. Cl.
CPC .............. *C08G 85/002* (2013.01); *C08K 5/05* (2013.01); *C08L 67/02* (2013.01)

(58) Field of Classification Search
CPC ....... C08G 85/002; C08J 2367/02; C08J 3/14; C08K 5/05; C08L 67/02
See application file for complete search history.

(56) References Cited

U.S. PATENT DOCUMENTS 5,665,808 A * 9/1997 Bilsbury .................. C08K 3/08
102/501
2004/0156911 A1 8/2004 Chattopadhyay et al.

* cited by examiner

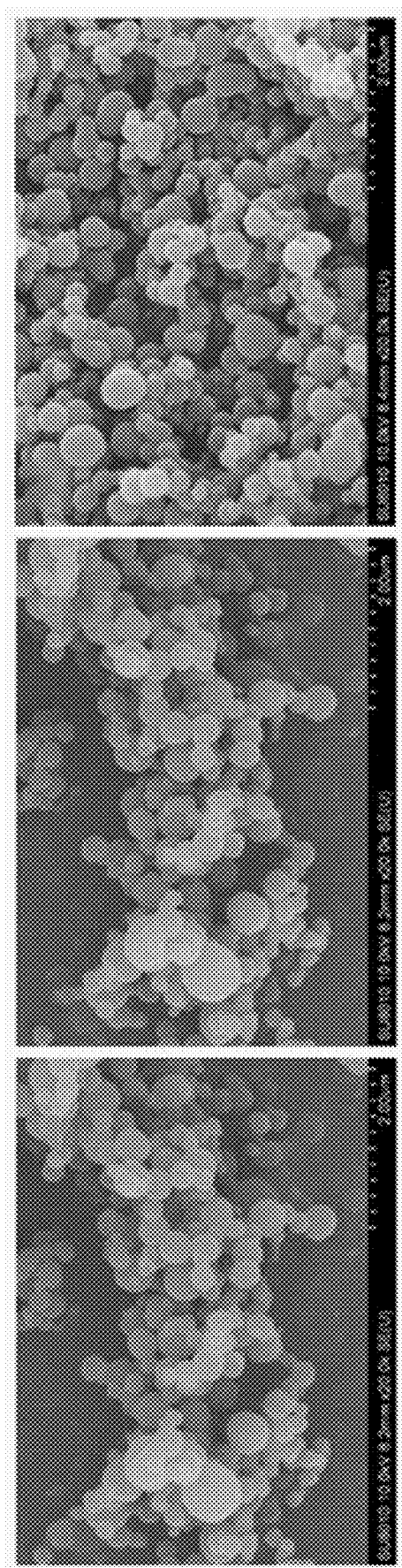
Fig. 4A
Fig. 4B
Fig. 4C
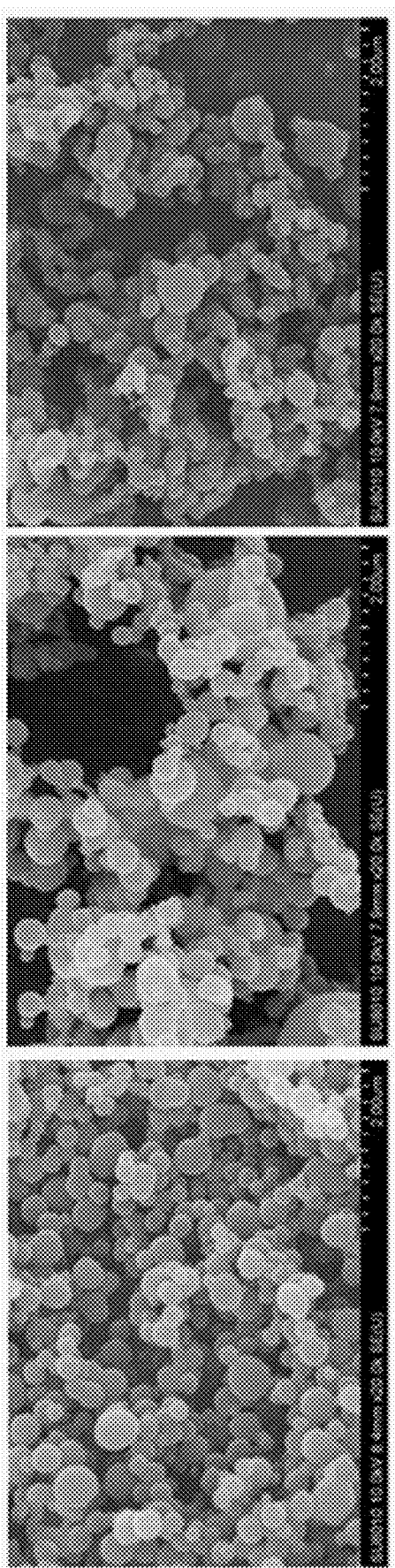
Fig. 4D
Fig. 4E
Fig. 4F

METHOD AND DEVICE FOR PURIFYING POLYBUTYLENE TEREPHTHALATE

CROSS-REFERENCE TO RELATED APPLICATION

This application claims priority to Taiwan Application Serial Number 106121301, filed Jun. 26, 2017, which is herein incorporated by reference.

BACKGROUND

Field of Invention

The present disclosure relates to a method and a device for purifying polybutylene terephthalate.

Description of Related Art

Currently, commercial polybutylene terephthalate (PBT) generally contains oligomers (e.g., cyclic oligomers), which are reacted incompletely, and a by-product of tetrahydrofuran (THF). However, the oligomers and THF may cause undesirable effects on the subsequent processes of the PBT, such as dyeing and injection molding processes. Therefore, there is a need for a method for effectively purifying PBT.

SUMMARY

A purpose of the present disclosure is to provide a method for effectively and rapidly purifying polybutylene terephthalate (PBT). It is possible to purify PBT by dissolving PBT with a low amount of oligomers and tetrahydrofuran (THF) in hexafluoroisopropanol (HFIP), and performing carbon dioxide ($CO_2$) anti-solvent method, and thus to precipitate PBT. The oligomers and THF are still dissolved in the HFIP to achieve the purpose of purifying the PBT.

The present disclosure provides a method for purifying PBT, which includes: providing or receiving initial PBT, in which the initial PBT includes oligomers; dissolving the initial PBT in hexafluoroisopropanol (HFIP) to form a PBT/HFIP solution, in which the oligomers are also dissolved in the HFIP; and contacting the PBT/HFIP solution with compressed $CO_2$ at a temperature and a pressure, thereby precipitating purified PBT, in which at least a portion of the oligomers are still dissolved in the HFIP, and the temperature is in a range of 20° C. to 35° C., and the pressure is in a range of 900 psi to 1400 psi.

According to some embodiments of the present disclosure, contacting the PBT/HFIP solution with the compressed $CO_2$ includes allowing the PBT/HFIP solution to form a plurality of droplets in the compressed $CO_2$.

According to some embodiments of the present disclosure, a weight percent of the initial PBT in the PBT/HFIP solution is in a range of about 1 wt % to about 8 wt %.

According to some embodiments of the present disclosure, contacting the PBT/HFIP solution with the compressed $CO_2$ includes precipitating a plurality of PBT particles, and each of the PBT particles having an average particle diameter in a range of about 0.1 microns to about 0.4 microns.

According to some embodiments of the present disclosure, contacting the PBT/HFIP solution with the compressed $CO_2$ at a temperature and a pressure includes introducing the PBT/HFIP solution into a high-pressure precipitation tank having the compressed $CO_2$.

According to some embodiments of the present disclosure, the method further includes cleaning the purified PBT using supercritical $CO_2$.

According to some embodiments of the present disclosure, the temperature is in a range of 22° C. to 26° C.

According to some embodiments of the present disclosure, the pressure is in a range of 1100 psi to 1300 psi.

According to some embodiments of the present disclosure, a weight percent of the initial PBT in the PBT/HFIP solution is in a range of 3 wt % to 6 wt %.

The present disclosure further provides a device for purifying PBT, which includes: a PBT/HFIP solution supply unit configured to supply a PBT/HFIP solution, in which the PBT/HFIP solution includes HFIP, PBT and oligomers of the PBT, and the PBT and the oligomers are dissolved in the HFIP; a $CO_2$ supply unit configured to supply compressed $CO_2$; a high-pressure precipitation tank connected to the PBT/HFIP solution supply unit and the $CO_2$ supply unit to respectively receive the PBT/HFIP solution and the compressed $CO_2$, in which the high-pressure precipitation tank is configured to allow the PBT/HFIP solution to be in contact with the compressed $CO_2$, thereby precipitating purified PBT, in which at least a portion of the oligomers is still dissolved in the HFIP.

It is to be understood that both the foregoing general description and the following detailed description are by examples, and are intended to provide further explanation of the invention as claimed.

BRIEF DESCRIPTION OF THE DRAWINGS

The invention can be more fully understood by reading the following detailed description of the embodiment, with reference made to the accompanying drawings as follows:

FIGS. 4A to 4F are scanning electron microscope (SEM) images of purified PBT particles according to Examples 22 to 27 of the present disclosure.

DETAILED DESCRIPTION

Figure 1:
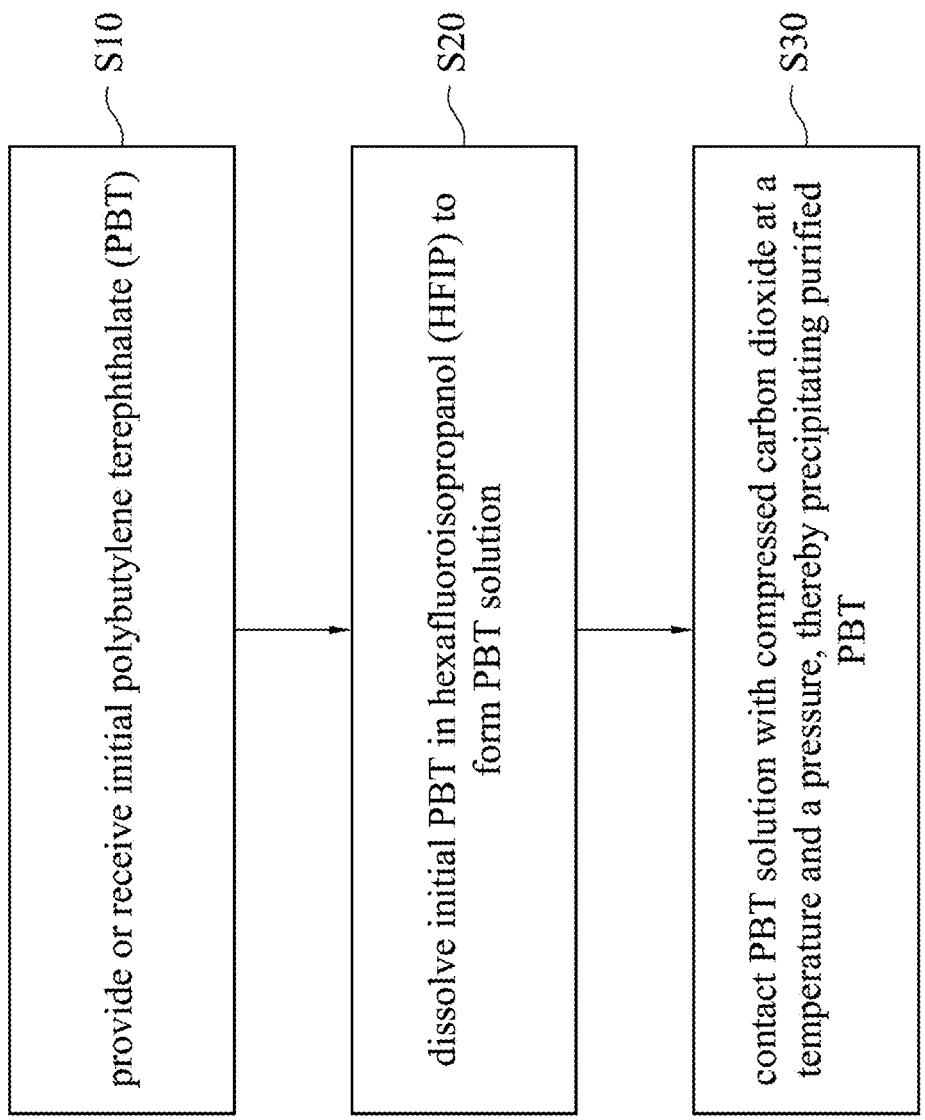
FIG. 1 is a flowchart of a method for purifying polybutylene terephthalate (PBT) according to some embodiments of the present disclosure.

In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing. As used herein, "around", "about" or "approximately" shall generally mean within 20 percent, preferably within 10 percent, and more preferably within 5 percent of a given value or range. Numerical quantities given herein are approximate; meaning that the term "around", "about" or "approximately" can be inferred if not expressly stated. It will be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present.

As mentioned above, currently, commercial polybutylene terephthalate (PBT) generally contains oligomers (e.g., cyclic oligomers), which are reacted incompletely, and a by-product of tetrahydrofuran (THF). The oligomers and THF may cause undesirable effects on the subsequent processes of the PBT, such as dyeing and injection molding processes. Among them, THF has low boiling point and low molecular weight and thus is easily removed, but oligomers have high molecular weights and thus are not easily removed.

Therefore, the present disclosure provides a method for effectively and rapidly purifying PBT. It is possible to purify PBT by dissolving PBT with a low amount of oligomers in hexafluoroisopropanol (HFIP), and performing carbon dioxide ($CO_2$) anti-solvent method, and thus to precipitate PBT, and most of the oligomers are still dissolved in the HFIP to achieve the purpose of purifying the PBT. Various embodiments of each operation of the method will be described in detail below.

FIG. 1 is a flowchart of a method for purifying polybutylene terephthalate (PBT) according to some embodiments of the present disclosure.

In operation S10, initial PBT particles are firstly provided or received, and the initial PBT particles contain oligomers, such as cyclic trimer and cyclic dimer. In some embodiments, the initial PBT particles contain about 0.5 to 3 wt % of the cyclic trimer and 0.1 to 1.5 wt % the cyclic dimer.

In operation S20, the initial PBT is dissolved in the HFIP to form a PBT/HFIP solution. The oligomers in the initial PBT particles are also dissolved in the HFIP to form the PBT/HFIP solution. In some embodiments, a weight percent of the PBT in the PBT/HFIP solution is less than or equal to 8 wt %, such as 7 wt %, 6 wt %, 5 wt %, 4 wt %, 3 wt %, 2 wt % or 1 wt %. In some embodiments, if the weight percent of the PBT is greater than a value, such as 8 wt %, the PBT precipitated in the subsequent operation will have irregular shape, which is not conducive to follow-up treatments and processes. In contrast, if the weight percent of the PBT is lower than a value, such as 1 wt %, overall efficiency is too low and thus is not economical. In some embodiments, the weight percent of the initial PBT in the PBT/HFIP solution is in a range of 3 wt % to 6 wt %. In some specific embodiments, the weight percent of the initial PBT in the PBT/HFIP solution is in a range of 3.7 wt % to 5.3 wt %.

Subsequently, $CO_2$ anti-solvent method is performed on the solution. Specifically, in operation S30, the PBT/HFIP solution is in contact with compressed $CO_2$ at a temperature and a pressure to precipitate PBT, and most or all of the oligomers are still dissolved in the HFIP. More specifically, when the solution is in contact with the compressed $CO_2$, the $CO_2$ rapidly diffuses into the PBT/HFIP solution to expand its volume. As such, solubility of the PBT in the HFIP is abruptly decreased, which causes the PBT to precipitate though nucleation and growth and thus to obtain purified PBT. At this time, most of cyclic oligomers are still dissolved in the HFIP and not precipitated. In some embodiments, 90 wt % to 99 wt % of the cyclic dimer is still dissolved in the HFIP and not precipitated. In some embodiments, 65 wt % to 85 wt % of the cyclic trimer is still dissolved in the HFIP and not precipitated.

In some embodiments, the operation S30 includes allowing the PBT/HFIP solution to form a plurality of droplets in the compressed $CO_2$.

In some embodiments, the PBT/HFIP solution is in contact with the compressed $CO_2$ for less than or equal to 1 minute to precipitate PBT. In some embodiments, the solution is in contact with the compressed $CO_2$ for less than 30 seconds, such as 25 seconds, 20 seconds, 15 seconds, 10 seconds or 5 seconds, to precipitate PBT. In other words, the process is extremely fast, and the process time is extremely short.

In some embodiments, the prepared purified PBT is granular. In some embodiments, the purified PBT is spherical or near-spherical. For example, the purified PBT has an average particle diameter of 0.05 microns to 2 microns, such as 0.2 microns, 0.3 microns, 0.4 microns, 0.5 microns, 0.6 microns, 0.7 microns, 0.8 microns or 0.9 microns. In some embodiments, the purified PBT has an average particle diameter in a range of about 0.1 microns to about 0.4 microns.

In some embodiments, the operation S30 includes introducing the PBT/HFIP solution into a high-pressure precipitation tank containing the compressed $CO_2$. The temperature and pressure described in the operation S30 are those in the high-pressure precipitation tank, which may also be referred to operating temperature and pressure, or system temperature and pressure.

In some embodiments, the operating pressure is in a range of 900 psi to 1400 psi, such as 1000 psi, 1100 psi, 1200 psi or 1300 psi. According to various embodiments of the present disclosure, the higher the operating pressure, the higher the expansion rate of the PBT/HFIP solution and the lower the solubility of the solute in the PBT/HFIP solution. When the operating pressure is greater than a value, such as greater than 1400 psi or 1300 psi, the cyclic oligomers may be precipitated together with the PBT, and thus fails to effectively purify PBT. In contrast, when the operating pressure is lower than a value, such as lower than 900 psi, the PBT in the PBT/HFIP solution may fail to be precipitated. Therefore, there is an appropriate operating pressure range of 900 psi to 1400 psi. In some embodiments, the operating pressure is in a range of 1100 psi to 1300 psi. In some specific embodiments, the operating pressure is in a range of 1066 psi to 1234 psi.

The operating temperature will affect volume expansion rate of the PBT/HFIP solution and the nucleation and precipitation rate of the PBT. In some embodiments, the operating temperature is in a range of 20° C. to 35° C., such as 21° C., 22° C., 23° C., 24° C., 25° C., 26° C., 27° C., 28° C., 29° C., 30° C., 31° C., 32° C., 33° C. or 34° C. In some embodiments, the operating temperature is in a range of 22° C. to 26° C. In some specific embodiments, the operating temperature is in a range of 23.4° C. to 31.7° C.

According to another embodiment of the present disclosure, the method further includes other operations or steps after the operation S30. In some embodiments, after the operation S30 is performed, the precipitated (purified) PBT is dried using the compressed $CO_2$. For example, introduction of the PBT/HFIP solution is stopped, and the compressed $CO_2$ is continuously supplied to remove the HFIP which may remain on the precipitated PBT. In other words, the pressure and the temperature of the drying operation may be same as or different from those of the operation S30.

Figure 2:
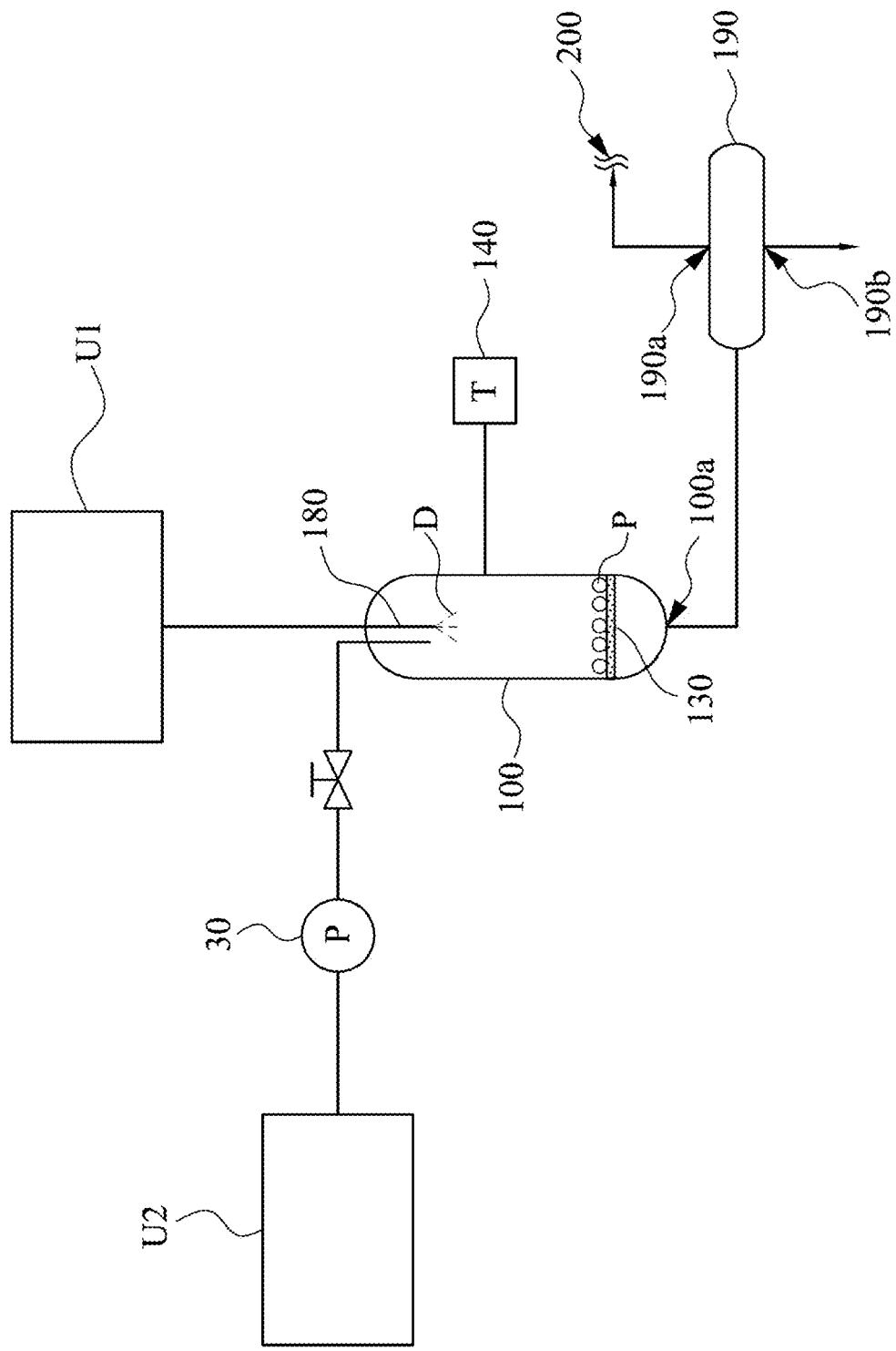
FIG. 2 is a schematic diagram of a device for purifying PBT according to some embodiments of the present disclosure.

FIG. 2 is a schematic diagram of a device for purifying PBT according to some embodiments of the present disclosure. As shown in FIG. 2, the device includes a high-pressure precipitation tank 100, a PBT/HFIP solution supply unit U1 and a $CO_2$ supply unit U2.

The PBT/HFIP solution supply unit U1 is connected to the high-pressure precipitation tank 100 and configured to supply PBT/HFIP solution into the high-pressure precipitation tank 100. The PBT/HFIP solution includes initial PBT and HFIP. The initial PBT includes oligomers dissolved in the HFIP.

In some embodiments, the device further includes a piping system (not shown), which is configured to supply the initial PBT and the HFIP into the PBT/HFIP solution supply unit U1.

In some embodiments, the high-pressure precipitation tank 100 further includes a nozzle 180 connected to the PBT/HFIP solution supply unit U1 via a piping line. The nozzle 180 is configured to eject the PBT/HFIP solution into the high-pressure precipitation tank 100 to form droplets D of the PBT/HFIP solution.

The $CO_2$ supply unit U2 is connected to the high-pressure precipitation tank 100 and configured to supply compressed $CO_2$ to the high-pressure precipitation tank 100. The droplets D of the PBT/HFIP solution in the high-pressure precipitation tank 100 are in contact with the compressed $CO_2$ and then expand, thereby precipitating purified PBT particles P, and most (or all) of the oligomers are still dissolved in the HFIP.

In some embodiments, the $CO_2$ supply unit U2 and the PBT/HFIP solution supply unit U1 are connected to a same side of the high-pressure precipitation tank 100 to allow the compressed $CO_2$ and the PBT/HFIP solution to flow along a substantially same direction, i.e., co-current operation. For example, as shown in FIG. 2, the $CO_2$ supply unit U2 and the PBT/HFIP solution supply unit U1 are connected to a top portion of the high-pressure precipitation tank 100. However, the present disclosure is not limited to the co-current operation, and an inlet of the compressed $CO_2$ and an inlet of the PBT/HFIP solution may be disposed at other positions of the high-pressure precipitation tank 100.

In some embodiments, the device further includes a pressure regulator 30 configured to control the pressure within the high-pressure precipitation tank 100. The pressure regulator 30 of FIG. 2 is connected between the $CO_2$ supply unit U2 and the high-pressure precipitation tank 100, but in other embodiments, the pressure regulator 30 may be disposed at an outlet of the high-pressure precipitation tank 100.

In some embodiments, the device further includes a temperature control device 140 to control the temperature within the high-pressure precipitation tank 100. In some embodiments, the temperature control device is connected to the high-pressure precipitation tank 100.

In some embodiments, the device further includes a filter device 130 disposed in the high-pressure precipitation tank 100. The filter device 130 is configured to collect the precipitated and purified PBT particles P. In some embodiments, the filter device 130 may include filters, filter bags and the like, and any suitable filter device may be applied to the embodiments of the present disclosure.

In some embodiments, the device further includes a gas-liquid separating device 190 connected to an outlet 100a of the high-pressure precipitation tank 100. The compressed $CO_2$, HFIP and oligomers are delivered from the outlet 100a to the gas-liquid separating device 190. In the gas-liquid separating device 190, the compressed $CO_2$ is converted to gaseous $CO_2$ and thus separated from the liquid HFIP and oligomers. For example, the pressure in the gas-liquid separating device 190 may be 1 to 20 atm. The gaseous $CO_2$ is delivered from an outlet 190a of the gas-liquid separating device 190 to the piping system 200 and then delivered back to the $CO_2$ supply unit U2. The liquid HFIP and oligomers are left from an outlet 190b of the gas-liquid separating device 190. In some embodiments, the outlet 190b of the gas-liquid separating device 190 is connected to another purification unit (not shown), which is configured to separate the HFIP from the oligomers and thus to obtain purified HFIP. The purified HFIP can be delivered to the PBT/HFIP solution supply unit U1 for use.

The following examples are provided to illustrate certain aspects of the present disclosure and to aid those of skill in the art in practicing this disclosure. These examples are in no way to be considered to limit the scope of the disclosure in any manner.

Analytical Method

First, contents of cyclic trimer and cyclic dimer in an initial PBT (Changchun Petrochemical Co., Ltd, 1200M) were obtained by the following method. The analytical method includes: dissolving the initial PBT into a mixing solvent including HFIP and chloroform and then heating to 50° C.; after lowering to ambient temperature, adding propionitrile thereto to precipitate polymer; after the polymer is completely precipitated, filtering supernatant and then analyzed by high performance liquid chromatography (HPLC). The initial PBT contained 1.58 wt % of the cyclic trimer and 0.48 wt % of the cyclic dimer, which were obtained by the above-mentioned analytical method.

Examples 1 to 21

Figure 3:
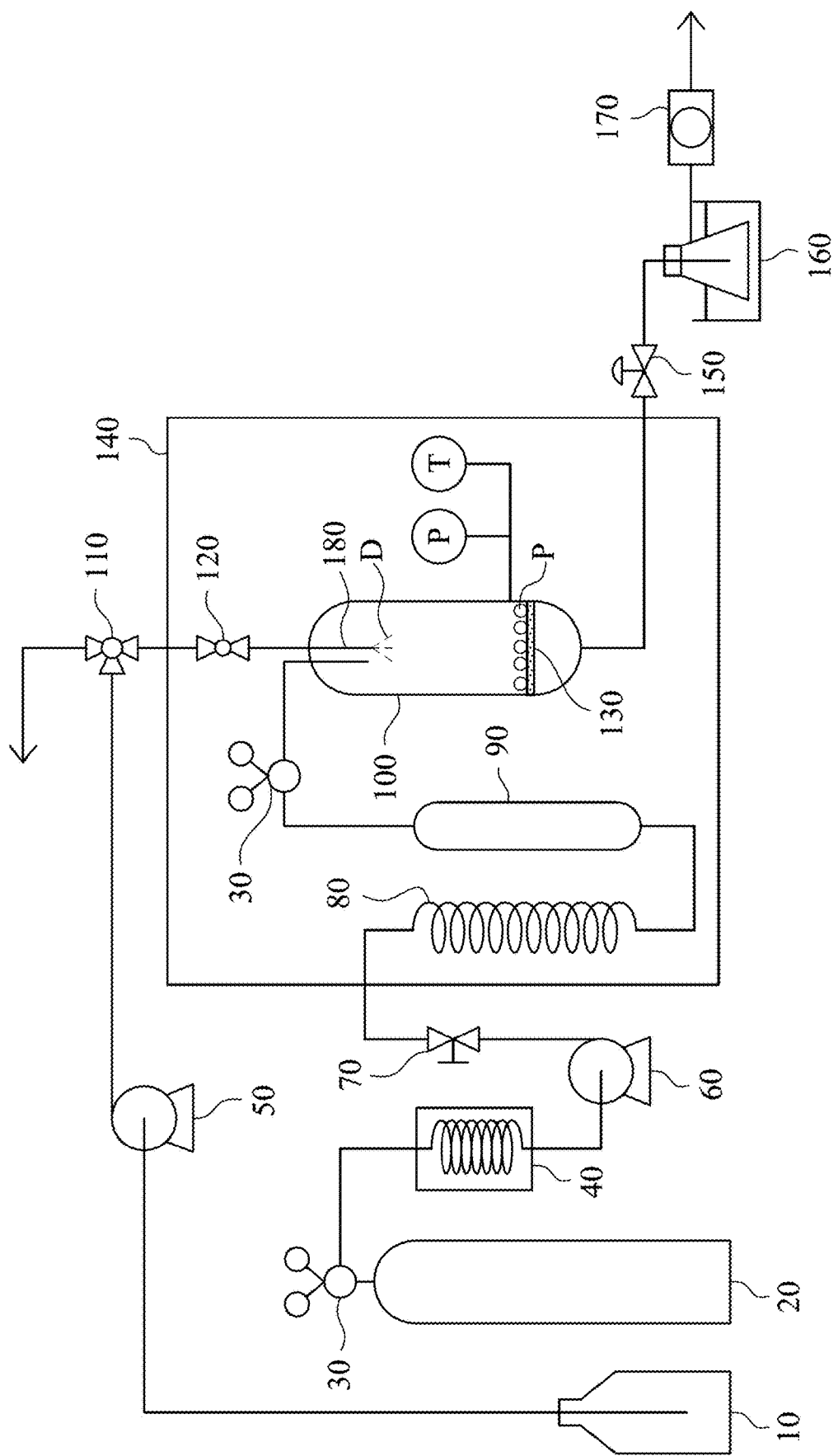
FIG. 3 is a schematic diagram of a device for purifying PBT according to Examples of the present disclosure.

The following examples were carried out using the device of FIG. 3. As shown in FIG. 3, the device includes a container 10, a $CO_2$ cylinder 20, a pressure regulator 30, a recirculating cooler 40, a high-pressure pump 50, a high-pressure pump 60, a valve 70, a preheater (e.g., a preheating coil) 80, a pressure tank 90, a high-pressure precipitation tank 100, a three-way valve 110, a balling valve 120, a filter device 130, an oven 140, a metering valve 150, an ice bath device 160, a gas flow meter 170 and a nozzle 180. The high-pressure pump 50 is an HPLC pump (LDC Analytical, USA, Constametric 3200). The high-pressure pump 60 is a high-pressure piston pump (Milton Roy, USA, MD46). The pressure tank 90 is a high-pressure tank (Whitey, USA, DOT-3A-1800), which can withstand 3000 psi. The high-pressure precipitation tank 100 has an inner diameter of 5 cm and a total volume of 600 ml, and the front and rear of the high-pressure precipitation tank 100 are provided with transparent windows. The gas flow meter 170 is a wet gas flow meter (Shinagawa, Japan, W-NK-1). The nozzle 180 is a capillary nozzle (Valco Instruments, USA), which has a length of 20 cm and an inner diameter of 0.25 mm.

The initial PBT was dissolved in the HFIP (Matrix, purity of 99.0%), and the cyclic trimer and cyclic dimer included therein were also dissolved in the HFIP, and thus to obtain the PBT/HFIP solution. The PBT/HFIP solution was then placed in the container 10 for later use.

The high-pressure precipitation tank 100 was disposed in the oven 140, which was used to control system temperature. During the procedure of the experiment, $CO_2$ (Lianhua gas, purity of 99.5%) was firstly delivered to the high-pressure tank 90, and flow rate was finally detected by the wet gas flow meter 170. After the system pressure and temperature and the flow rate of $CO_2$ were stabilized, the PBT/HFIP solution was delivered by the high-pressure pump 50 and sprayed into the high-pressure precipitation tank 100 through the nozzle 180 to form a plurality of droplets D. The droplets D was supersaturated in a very short time, thereby precipitating PBT particles P, and the PBT particles P were then collected by the filter device 130.

After the PBT/HFIP solution was sprayed, $CO_2$ with a flow rate of 2 L/min was continuously supplied to the high-pressure precipitation tank 100 for 3 hours to dry the precipitated PBT particles P. Thereafter, the precipitated PBT particles were obtained, and content of the cyclic trimer of the PBT particles was measured by the above-mentioned analytical method of the cyclic oligomers to calculate removal rate of the cyclic trimer. The experimental conditions and the removal rates of the cyclic trimer of Examples 1 to 20 are listed in Table 1.

TABLE 1

|  | pressure (psi) | temperature (° C.) | PBT/HFIP solution concentration (wt %) | removal rate of cyclic trimer (%) |
| --- | --- | --- | --- | --- |
| Example 1 | 1100 | 25.0 | 4.0 | 72.1 |
| Example 2 | 1200 | 25.0 | 4.0 | 78.6 |
| Example 3 | 1100 | 30.0 | 4.0 | 68.6 |
| Example 4 | 1200 | 30.0 | 4.0 | 72.0 |
| Example 5 | 1100 | 25.0 | 5.0 | 72.6 |
| Example 6 | 1200 | 25.0 | 5.0 | 79.0 |
| Example 7 | 1100 | 30.0 | 5.0 | 68.8 |
| Example 8 | 1200 | 30.0 | 5.0 | 72.1 |
| Example 9 | 1066 | 27.5 | 4.5 | 68.4 |
| Example 10 | 1234 | 27.5 | 4.5 | 75.0 |
| Example 11 | 1150 | 23.4 | 4.5 | 74.6 |
| Example 12 | 1150 | 31.7 | 4.5 | 69.2 |
| Example 13 | 1150 | 27.5 | 3.7 | 74.4 |
| Example 14 | 1150 | 27.5 | 5.3 | 74.5 |
| Example 15 | 1150 | 27.5 | 4.5 | 74.8 |
| Example 16 | 1150 | 27.5 | 4.5 | 74.2 |
| Example 17 | 1150 | 27.5 | 4.5 | 74.7 |
| Example 18 | 1150 | 27.5 | 4.5 | 74.3 |
| Example 19 | 1150 | 27.5 | 4.5 | 74.5 |
| Example 20 | 1150 | 27.5 | 4.5 | 74.7 |

It is noted that the main cyclic oligomer in the PBT was the cyclic trimer. Therefore, if there was a high removal rate of the cyclic trimer, it was reasonable to conclude that the cyclic dimer with lower molecular weight might have a higher removal rate.

The experimental conditions of Examples 1 to 20 were designed by an experimental design-reaction surface method including $2^3$-factor design, 6-axis point experiment and 3-center point experiment to examine effects of the pressure and temperature of $CO_2$ and the concentration of the PBT/HFIP solution on the removal rate of the cyclic trimer. In addition, analysis of variance (ANOVA) of experimental design was performed on those experimental results, which is listed in Table 2.

TABLE 2

|  | Degrees of freedom | Sum of square | Mean square | F-value | p-value |
| --- | --- | --- | --- | --- | --- |
| Regression | 9 | 160.79 | 17.87 | 36.90 | 0.000 |
| Linear | 3 | 135.32 | 45.11 | 93.17 | 0.000 |
| Pressure | 1 | 68.56 | 68.56 | 141.62 | 0.000 |
| Temperature | 1 | 66.56 | 66.56 | 137.48 | 0.000 |
| Concentration | 1 | 0.20 | 0.20 | 0.40 | 0.539 |
| Interaction | 3 | 4.67 | 1.56 | 3.22 | 0.071 |
| Pressure × Temperature | 1 | 4.65 | 4.65 | 9.61 | 0.011 |
| Pressure × $CO_2$ flow rate | 1 | 0.01 | 0.01 | 0.02 | 0.882 |
| Temperature × $CO_2$ flow rate | 1 | 0.01 | 0.01 | 0.02 | 0.882 |
| Residual Error | 10 | 4.84 | 0.48 |  |  |
| Lack-of-Fit | 5 | 4.55 | 0.91 | 1.57 | 0.125 |
| Pure Error | 5 | 0.29 | 0.06 |  |  |

After the influencing factor was found, polynomial regression model was obtained by calculating using Minitab 16. The regression model equation was:

$$Y=74.44+2.24X_1-2.21X_2+0.12X_3-0.92X_{12}-0.83X_{22}+0.07X_{32}-0.08X_1X_2-0.04X_1X_3-0.04X_2X_3,$$
$$R^2=0.952.$$

An optimum experimental operating condition was obtained by calculating this regression model, that the pressure was 1200 psi, and the temperature is 23.4° C., and the PBT/HFIP solution concentration was 4.5 wt %, and the predicted removal rate of the cyclic trimer was 80.2 wt %.

In order to confirm prediction accuracy of the removal rate of the cyclic trimer, an experiment with operating pressure of 1200 psi, operating temperature of 23.4° C. and PBT/HFIP solution concentration of 4.5 wt % was performed using the device and the procedure same as those of Examples 1 to 20. Next, content of the cyclic trimer of the PBT particles was measured by the above-mentioned analytical method to calculate removal rate of the cyclic trimer. The experimental condition, actual removal rate of the cyclic trimer and error between the actual removal rate and the predicted removal rate are listed in Table 3.

TABLE 3

|  | pressure (psi) | temperature (° C.) | PBT/HFIP solution concentration (wt %) | removal rate of cyclic trimer (%) | error (%) |
| --- | --- | --- | --- | --- | --- |
| Example 21 | 1200 | 23.4 | 4.5 | 81.4 | 1.47 |

As shown in Table 3, the actual removal rate of the cyclic trimer was 81.4 wt %, which was close to the predicted removal rate, and thus to confirm that the regression model had high reliability.

In addition, actual removal rate of the cyclic dimer of Example 21 was measured, which is 95.7 wt %. It confirmed that when there was a high removal rate of the cyclic trimer, the cyclic dimer with lower molecular weight will have a higher removal rate.

Examples 22 to 27

Purified PBT particles were obtained by performing the experiment with a $CO_2$ feed volume flow rate of 10 ml/min and experimental conditions of Table 4 using the device and the procedure same as those of Examples 1 to 21. Next, the purified PBT was analyzed by scanning electron microscope (SEM).

TABLE 4

|  | pressure (psi) | temperature (° C.) | PBT/HFIP solution concentration (wt %) |
| --- | --- | --- | --- |
| Example 22 | 1000 | 25.0 | 5.0 |
| Example 23 | 1100 | 25.0 | 5.0 |
| Example 24 | 1200 | 25.0 | 5.0 |
| Example 25 | 1300 | 25.0 | 5.0 |
| Example 26 | 1200 | 27.5 | 5.0 |
| Example 27 | 1200 | 30.0 | 5.0 |

FIGS. 4A to 4F are scanning electron microscope (SEM) images of purified PBT particles according to Examples 22 to 27 of the present disclosure. As shown in FIGS. 4A to 4F, under the operating pressure in a range of 1000 to 1300 psi and the operating temperature in a range of 25 to 30° C., the precipitated and purified PBT particles were spherical.

The PBT particles of Examples 22 to 27 respectively had average particle diameters of 254 nm, 239 nm, 246 nm, 233 nm, 241 nm and 259 nm. A standard deviation of the average particle diameters of the PBT particles of Examples 22 to 27 was within 10%.

As mentioned above, the present disclosure does provide a method for effectively purifying PBT, which is able to effectively remove cyclic oligomers therein. In addition, the process has short operation time, low energy consumption and is environmentally-friendly, and thus has industrial application value.

The foregoing outlines features of several embodiments so that those skilled in the art may better understand the aspects of the present disclosure. Those skilled in the art should appreciate that they may readily use the present disclosure as a basis for designing or modifying other processes and structures for carrying out the same purposes and/or achieving the same advantages of the embodiments introduced herein. Those skilled in the art should also realize that such equivalent constructions do not depart from the spirit and scope of the present disclosure, and that they may make various changes, substitutions, and alterations herein without departing from the spirit and scope of the present disclosure.

What is claimed is:

1. A method for purifying polybutylene terephthalate (PBT), comprising:
   providing or receiving initial PBT, wherein the initial PBT comprises oligomers;
   dissolving the initial PBT in hexafluoroisopropanol (HFIP) to form a PBT/HFIP solution, wherein the oligomers are dissolved in the HFIP, wherein a weight percent of the initial PBT in the PBT/HFIP solution is in a range of about 1 wt % to about 8 wt %; and
   contacting the PBT/HFIP solution with compressed carbon dioxide ($CO_2$) at a temperature of 20° C. to 35° C. and a pressure of 900 psi to 1400 psi, thereby precipitating purified PBT at the temperature and the pressure, wherein at least a portion of the oligomers are still dissolved in the HFIP.

2. The method of claim 1, wherein contacting the PBT/HFIP solution with the compressed $CO_2$ comprises:
   allowing the PBT/HFIP solution to form a plurality of droplets in the compressed $CO_2$.

3. The method of claim 1, wherein contacting the PBT/HFIP solution with the compressed $CO_2$ comprises:
   precipitating a plurality of PBT particles, and each of the PBT particles having an average particle diameter in a range of about 0.1 microns to about 0.4 microns.

4. The method of claim 1, wherein contacting the PBT/HFIP solution with the compressed $CO_2$ at the temperature and the pressure comprises:
   introducing the PBT/HFIP solution into a high-pressure precipitation tank containing the compressed $CO_2$.

5. The method of claim 1, further comprising:
   drying the purified PBT using supercritical $CO_2$.

6. The method of claim 1, wherein the temperature is in a range of 22° C. to 26° C.

7. The method of claim 1, wherein the pressure is in a range of 1100 psi to 1300 psi.

8. The method of claim 1, wherein a weight percent of the initial PBT in the PBT/HFIP solution is in a range of 3 wt % to 6 wt %.

* * * * *